United States Patent [19]

Kimura et al.

[11] Patent Number: 5,131,777
[45] Date of Patent: Jul. 21, 1992

[54] SPRING BIASED LIQUID APPLICATOR WITH INTEGRAL REMOVABLE CAP

[75] Inventors: Kimura Junji, Shigeki Suzuki, both of Tokyo, Japan

[73] Assignee: Terumo Kabushiki Kaisha, Tokyo, Japan

[21] Appl. No.: 476,503

[22] PCT Filed: Dec. 7, 1988

[86] PCT No.: PCT/JP88/01234
§ 371 Date: Jun. 11, 1990
§ 102(e) Date: Jun. 11, 1990

[87] PCT Pub. No.: WO89/05695
PCT Pub. Date: Jun. 29, 1989

[30] Foreign Application Priority Data

Dec. 15, 1987 [JP] Japan .............. 62-315251

[51] Int. Cl.⁵ .............................. A45D 34/00
[52] U.S. Cl. ................... 401/202; 401/132; 401/148; 401/180; 401/206; 401/264
[58] Field of Search ............. 401/148, 180, 205, 206, 401/132, 264, 202

[56] References Cited

U.S. PATENT DOCUMENTS

| | | | |
|---|---|---|---|
| 395,905 | 1/1889 | Jensen | 401/264 |
| 1,315,305 | 9/1919 | Hegland | 401/148 |
| 2,097,266 | 10/1937 | Vosbikian et al. | 401/206 |
| 2,418,035 | 3/1947 | Lachapelle | 401/148 |
| 3,377,124 | 4/1968 | Matsumoto | 401/206 X |
| 3,463,597 | 8/1969 | Wakai | 401/206 |
| 3,468,611 | 9/1969 | Ward | 401/206 X |
| 3,661,666 | 5/1972 | Foster et al. | |
| 4,225,253 | 9/1980 | Fraleigh | 401/148 X |
| 4,269,527 | 5/1981 | Lipfert | 401/180 X |
| 4,334,638 | 6/1982 | Stock. | |
| 4,480,940 | 11/1984 | Woodruff | 401/148 X |
| 4,890,944 | 1/1990 | Cousins et al. | 401/132 X |

FOREIGN PATENT DOCUMENTS

| | | |
|---|---|---|
| 3937030A1 | 5/1990 | Fed. Rep. of Germany . |
| 57-184781 | 5/1956 | Japan . |
| 57-55862 | 4/1982 | Japan . |
| 838800 | 6/1960 | United Kingdom . |

*Primary Examiner*—Steven A. Bratlie
*Attorney, Agent, or Firm*—Frishauf, Holtz, Goodman & Woodward

[57] ABSTRACT

A container of a liquid applicator containing a liquid, and an applicator member is held on the container for applying the liquid to an objective part. The applicator member is mounted for movement into and out of the container and a biasing member is provided to bias the applicator member outwardly of the container. When the applicator member is pressed into the container against the force of the biasing member, the liquid is caused to exude to the surface of the applicator member outside the container. Therefore, it is possible to provide a liquid applicator which has a container of any desired volume and made of a rigid and hard material and which allows only the liquid to exude to the outer surface of the container and be spread properly and effectively over an objective part.

12 Claims, 3 Drawing Sheets

FIG.I(A)
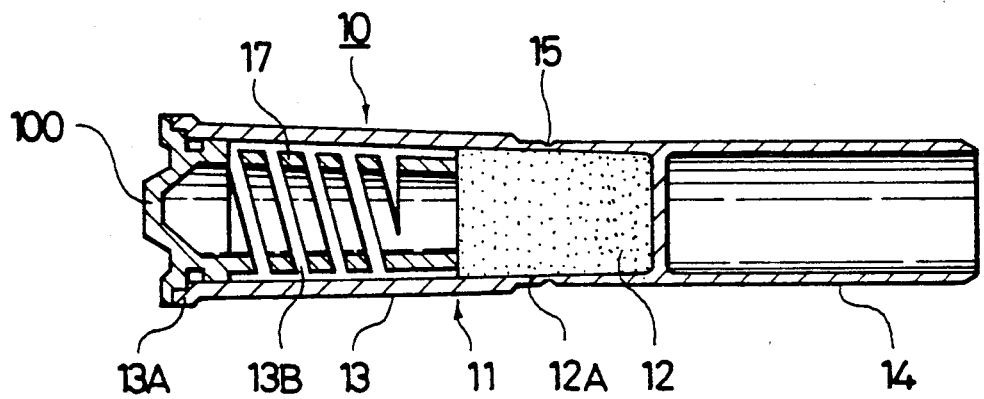
FIG.I(B)
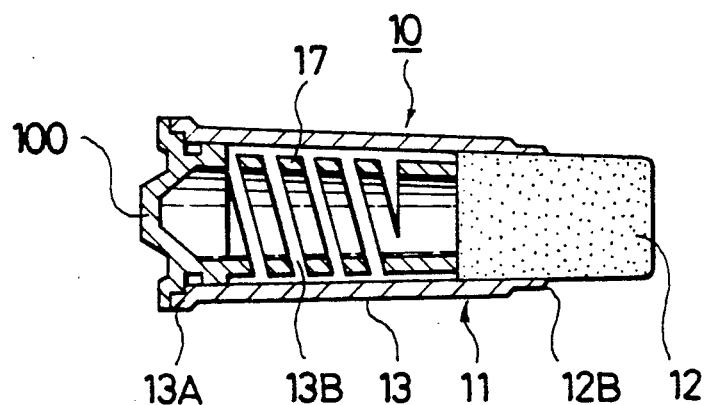
FIG.I(C)
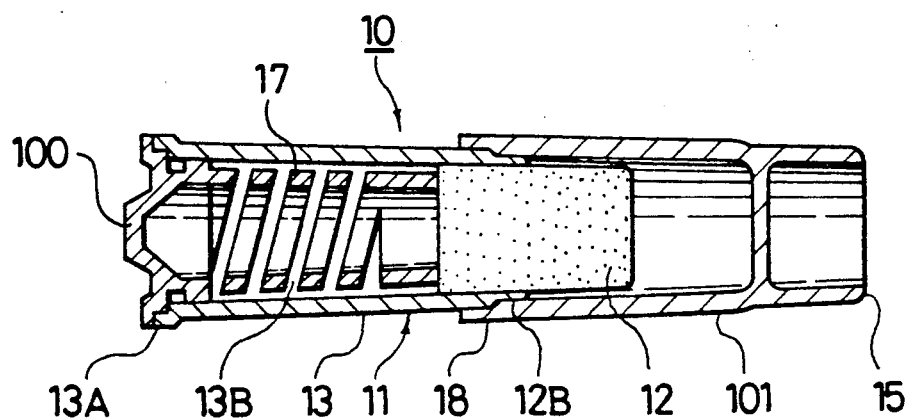

SPRING BIASED LIQUID APPLICATOR WITH INTEGRAL REMOVABLE CAP

BACKGROUND OF THE INVENTION

The present invention relates to a liquid applicator which contains a small quantity of a liquid used for medical, cosmetic, office, cooking, mechanical processing, or cleaning purpose and which has an applicator member, the applicator being capable of properly and effectively applying such a liquid to an objective part of a living body, office paper, coking instrument, machine or a cleaning object.

Hitherto, medical liquid applicators have been known which include containers for containing the liquid and applicator members associated with the containers. There are two types of such medical liquid applicators: a type in which a brush is provided on the cap of the container and a type having an applicator member held on the container. The applicator incorporating a brush is difficult to handle and is disadvantageous in that the bristles of the brush tend to stimulate an affected part of the living body. On the other hand, the second-mentioned type requires that the container can be deformed to enable the liquid to be squeezed out of the applicator member, through this type of liquid applicator can be handled more easily. Therefore, most of the known medical liquid applicators comprise a container made of a deformable material, e.g., a plastic, and an applicator member fixed on the container.

In the medical liquid applicator of the type mentioned above, since the container material is limited to a deformable material such as a plastic which enables squeezing out the liquid, it is not possible to use a glass as the container material, despite that the glass exhibits various advantages such as resistance to a serialization process, prevention of scattering of volatile solvent or volatile agent, prevention of absorption of medicine, and so forth.

Furthermore, in order that the container having a small volume can exhibit the deformability particular to the materials, it is necessary that the container wall has a smaller wall thickness as compared with containers of large volume or that the container material is soft and flexible. The ratio between the surface area of the container and the volume of the container varies in inverse proportion to the ⅓ order of the volume, so that the ratio of the surface area to the volume increases as the volume is decreased. This means that containers of smaller volume exhibit a greater rate of evaporation/scattering of the liquid per unit volume. For instance, in order for a small container having a volume of 1 ml to exhibit the same rate of evaporation/scattering as that of a container having a volume of 10 ml, it is necessary that the smaller container have a wall thickness which is 2.15 times as large as that of the greater container or, alternatively, that the smaller container is made of a material having lower permeability and, hence, a higher rigidity. Thus, production of a container having a small volume and large deformability is encountered with a problem in that two incompatible requirements must be met simultaneously: namely, the use of a thinner or more flexible material than that of the large container to provide large deformability and the use of thickener and more rigid material to prevent evaporation/scattering. It is therefore difficult to reduce the volume of the container of the conventional medical liquid applicator having an applicator member fixed on the container, in order to prevent evaporation/scattering of the liquid.

JP.U.57-184781 discloses an applicator in which an end valve with an applicator member fixed to one end thereof is held in pressure contact with the opening of a liquid chamber such that the applicator member projects from the body of the applicator. In this known applicator, when the liquid is applied by the applicator member, the end valve is pressed to keep the opening of the applicator chamber open to allow the liquid to be discharged continuously, so that an excess amount of liquid is dispensed. This known liquid applicator, therefore, cannot apply the liquid in such a manner that only a predetermined quantity of liquid exudes and be spread into a very thin film of the liquid.

An object of the present invention is to provide a liquid applicator which has a container of any desired volume and made of a rigid and hard material and which allows only a predetermined quaintly of the liquid to exude to the outer surface of the container and be spread properly and effectively over an objective part.

SUMMARY OF THE INVENTION

According to the present invention, a liquid applicator comprises a container containing a liquid and an applicator member held on the container and capable of applying the liquid to an objective part, wherein the applicator member is mounted for movement into and out of the container and a biasing member is provided to bias the applicator member outwardly of the container, such that when the applicator member is pressed into the container against the force of the biasing member so as to reduce the internal volume of the container, the liquid in an amount corresponding to the reduction in the internal volume of the container is caused to exude to the surface of the applicator member outside the container.

Another feature of the present invention is that the container includes a container body containing the liquid and made of a glass and/or a hard plastic so as to have an openable end, and a cap capable of hermetically closing the opening of the container body, wherein the applicator member is held on the container body such that a portion of the applicator member is exposed through the opening in the container body.

Another feature of the present invention is that the container includes a container body containing the liquid and made of a glass and/or a hard plastic so as to have an openable end, and a sealing member for sealing the end of the container body, the sealing member and the container body being integrally formed in such a manner that they can be separated when the liquid applicator is put to use, the applicator member being held on the container body such that a portion of the applicator member is exposed through the openable end which is opened after separation of the sealing member from the container body.

Another feature of the present invention is that the biasing member is housed in the container body.

Another feature of the present invention is that the applicator member may be made of a material permeable to the liquid.

Another feature of the present invention is that the container body and the sealing member are formed integrally with each other and a breakable thin-walled portion is formed between the container body and the sealing member.

Another feature of the present invention is that the end of the sealing member opposite to the end where the sealing member is integrated with the container body is so shaped as to fit to the container body after the sealing member is separated from the container body.

Another feature of the present invention is that the container has an ointment storage portion.

Still another feature of the present invention is that the liquid applicator internal volume of the container is caused to exude to the surface of the applicator member outside the container, the liquid applicator further comprises a liquid dripping member having a cap-type member with a small port for dripping the liquid formed in the end thereof, the dripping member being fitted on the container with the applicator member held therein so as to allow the applicator member to move into and out of the container.

According to the present invention, the outer surface of the applicator member is simply pressed onto the objective portion so that the applicator member is pressed into the container overcoming the biasing force of the biasing member so as to reduce the internal volume of the container, whereby only an amount of liquid corresponding to the reduction in the volume is caused to exude to the outer surface of the applicator through the applicator member.

It is therefore possible to apply the liquid without relying upon the deformability of the container. This means that rigid and hard material such as a glass and/or a hard plastic can be used effectively as the material of the container. It is also possible to obtain an applicator having a container of a small volume and made of a plastic the thickness or rigidity of which being determined to provide sufficient evaporation/scattering prevention effect, enabling smooth exudation of the liquid to the outer surface of the applicator member.

The amount of the liquid which exudes to the outer surface of the applicator member is limited to the amount corresponding to the reduction in the internal volume of the vessel caused by pressing of the applicator member into the container. This means that the amount of exuding liquid can be controlled by adjusting the position or amount of pressing of the applicator member into the container, because the reduction in the internal volume of the container ceases when the pressing of the applicator member is stopped. It is therefore possible to apply a desired amount of liquid in the form of a thinly spread film.

When the container is formed of a glass or a hard plastic, advantages are brought about such as high resistance to treatment in the serialization process, prevention of evaporation/scattering of volatile solvent and volatile medical agent, prevention of absorption of medical agent, and so forth.

When a container of small volume is used in the liquid applicator of the present invention, the material and the thickness of the container can be determined mainly from the view point of prevention of evaporation and absorption of the medical agent, without taking into consideration the deformability of the container. Thus, the container can be designed freely by using general-purpose polymers having small moisture permeation and small agent absorption, e.g., high-density polyethylene (HDPE) and polypropylene (PP) which are generally rigid and, hence, have no deformability.

The applicator member in the liquid applicator of the present invention is formed of a material which exhibits a large permeability to the liquid agent, e.g., cotton, non-woven cloth, paper, fibrous filter, bundle of long fibers and porous plastic.

Examples of the liquid which is contained in the liquid applicator of the present invention are liquid agents which are applied to human skin for the purpose of disinfection or medical care, cosmetic liquids, liquids such as adhesives to be applied to papers for office use, liquid such as oils to be applied to cooking instruments, liquids such a lubricants to be applied to machines, and liquids such as waxes to be applied to objects which are to be cleaned.

Obviously, the present invention can be carried out in various forms, using the containers of glass or had plastic and containers of small volume which are specifically mentioned.

Using a liquid dropping member which covers part of whole of the applicator member, when the dripping member covers the entire area of the applicator member, the dripping member is provided with at least one communication hole. In use, the dripping member is fitted on the applicator member and is pressed so as to cause the liquid to be dripped onto the objective portion. The dripping member may be used in combination with the other liquid applicator features described above.

BRIEF DESCRIPTION OF THE DRAWINGS

FIG. 1(A) is a sectional view of an embodiment of the present invention;

FIG. 1(B) is a sectional view showing the state of use;

FIG. 1(C) is a sectional view showing the state of use with a modified cap attached to the applicator;

DETAILED DESCRIPTION

First Embodiment

Figure 2:
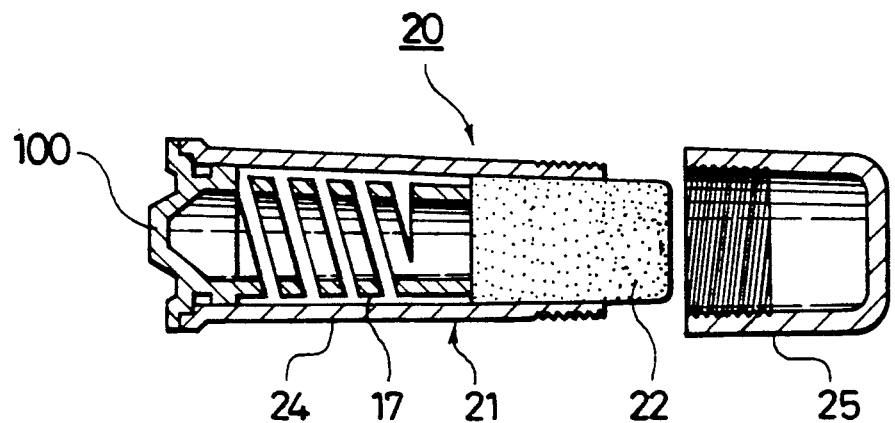
FIG. 2 is a sectional view of a second embodiment of the present invention.

A medical liquid applicator 10 shown in FIGS. 1(A) to 1(C) comprises a container 11 containing a liquid agent for medical care and an applicator member 12 which is held by the container 11 and capable of applying the liquid agent to a part of a living body.

The container 11 includes a container body 13 for containing the liquid agent, the container body 13 being made of a glass and/or a hard plastic and which is provided with an end 12A which can be opened (see FIG. 1(A)), and a sealing member 14 for sealing the end 12A. The container body 13 has a bottom plate 100 welded to the bottom portion 13A so as to form a liquid agent containing portion 13B.

The sealing member 14 and the container body 13 are formed integrally with each other through a structure which enables the sealing member 14 to be separated from the container body 13, e.g., a thin-walled portion 15 (0.3 to 0.5 mm thick) forming a V-shaped recess. In use, the user pinches or grips the container body 13 and the sealing member 14 by the user's hands and applies a force so as to break the connection between the container body 13 and the sealing member 14 at the thin-walled portion 15 thereby separating the sealing member 14 from the container body 13. The container 11 is designed such that the applicator member 12 is held on the container body 13 such that a portion of the applicator member 12 is exposed through an open end 12B (see FIG. 1(B)) of the container body 13 after the separation of the sealing member 14.

The applicator member 12 is mounted so as to be movable into and out of the container body 13.

The medical liquid agent applicator 10 further has a spring biasing 17 which biases the applicator member 12 outwardly of the container 11. For instance, the spring 17 is formed from a plastic integrally with the bottom plate 100 and is accommodated in the liquid containing portion 13B of the container body 13 at a position between the applicator member 12 and the bottom plate 100. The applicator member 12 which receives the resilient urging force of the spring 17 is prevented from springing out of the container because its peripheral edge portion is retained by a tapered inner surface of the container body 13 and because its base end is connected to the spring 17. After the separation of the sealing member 14 from the container body 13, the liquid applicator 10 is ready for use. In this case, as the applicator member 12 is pressed into the liquid containing portion 13B of the container body 13 against the force of the spring 17, the liquid agent is caused to exude to the outer surface of the applicator member 12 exposed from the container.

The applicator member 12 is preferably made of a material which is highly permeable to and inactive on the liquid agent and which has a good shape holding characteristic, as well as an ability to impart a good feel of contact when pressed to a human skin. It is also preferred that the material of the applicator member 12 has a resistance to breakage so as not to produce fractions. For instance, a generally cylindrical bundle of a multiplicity of acetyl cellulose long fibers bonded together is suitably used as the applicator member. It is also possible to use a porous material as the material of the liquid applicator 12.

As is the case of a sealing member 101 shown in FIG. 1(C), the sealing member may be provided at its end opposite to the container body 13 with a fitting portion 18 which is adapted to fit on the open end 12B of the container body 13 after the severance of the sealing member from the container body 13 so as to function as a cap.

The described medical liquid agent applicator 10 can be assembled by the following procedure. The applicator member 12 is inserted into the structure comprised of the container body 13 and the sealing member 14 from the end adjacent to the bottom plate 100. Then, after filling the container body 13 with the liquid agent, the spring 17 integral with the bottom plate is inserted and then the bottom plate 100 is welded to the bottom portion 13A of the container body 13.

A description will now be given of the operation of the medical liquid agent applicator 10.

According to this applicator 10, the applicator member 12 is pressed into the container against the force of the spring 17 simply by being pressed at its outer surface onto an affected part of the living body with a light force, so that the internal pressure of the container is increased to cause the liquid agent in the container to be exuded to the surface of the applicator member 12 outside the container.

It is therefore possible to easily apply the liquid agent without relying upon the deformability of the container. Thus, the liquid agent in the container 11 can smoothly exude to the surface of the applicator member 12 outside the container even when the container is made of a rigid and hard material such as a glass and/or a hard plastic and even when the container is a small-size container having a thickness and rigidity large enough to provide an anti-evaporation/scattering function.

It is also to be understood that the amount of the liquid which exudes to the surface of the applicator member 12 is limited to the amount which corresponds to the reduction in the internal volume of the container caused by the pressing of the applicator member 12 into the container. Therefore, if the amount of movement of the applicator member 12 into the container is limited, the amount of reduction in the internal volume of the container also is limited, thus making it possible to control the amount of exuding liquid to a constant value and hence, to apply a predetermined amount of liquid in the form of a thinly spread film.

Figure 3:
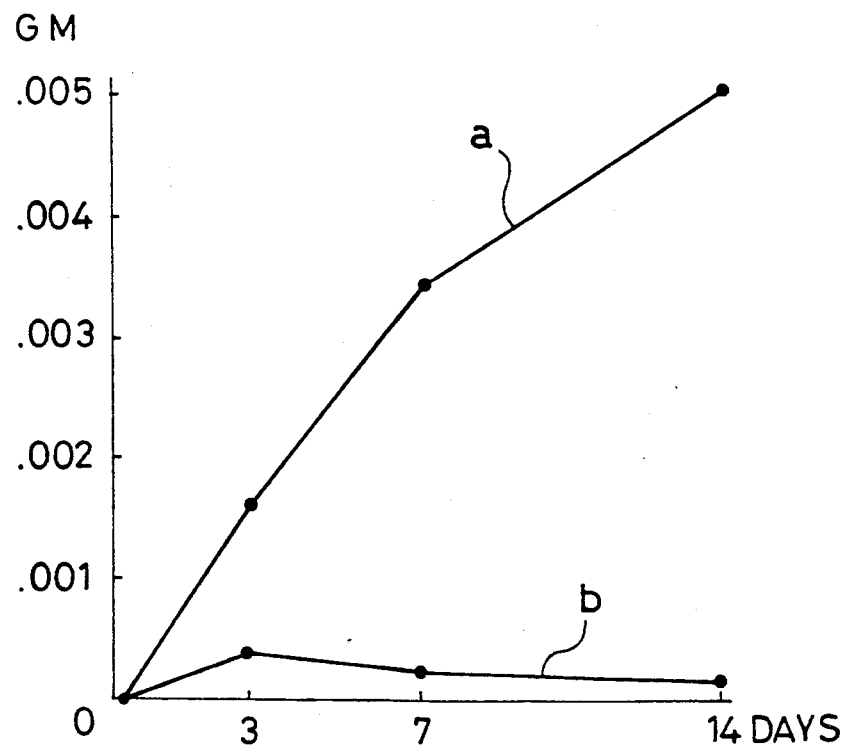
FIG. 3 is a diagram illustrating the relationship between the deformability of the container and evaporation/scattering prevention function of the container.

FIG. 3 shows the relationship between the deformability of the container and the evaporation/scattering prevention function. In this Figure, the abscissa represents the number of days elapsed, while the ordinate represents the amount of evaporation/scattering of distilled water when the same is held at 40° C. curve (a) represents a characteristic which is obtained when the container is a deformable container with a pipette type cap, while a curve (b) shows the characteristic as obtained with a container which is sealed with a polypropylene of 1 mm thick and which has no deformability.

Second Embodiment

A medical liquid agent applicator 20 shown in FIG. 2 has a container 12 and an applicator member 22, as in the case of the applicator 10 described before. The applicator member 22 is mounted for movement into and out of the container 21 and is outwardly biased by the spring 17 which is integral with the bottom plate 100. The liquid agent in the container 21 is caused to exude to the surface of the applicator member 22 outside the container as the applicator member 22 is pressed into the container 21 against the force of the spring 17.

The container 21 of the applicator 20 includes a container body 24 containing the liquid agent and made from a glass and/or a hard plastic so as to have an opening, and a cap 25 which can hermetically close the opening of the container body 24. The applicator member 22 is mounted on the container body 24 such that it is exposed from the opening of the container body 24 when the cap 25 is removed.

Third Embodiment

Figure 4:
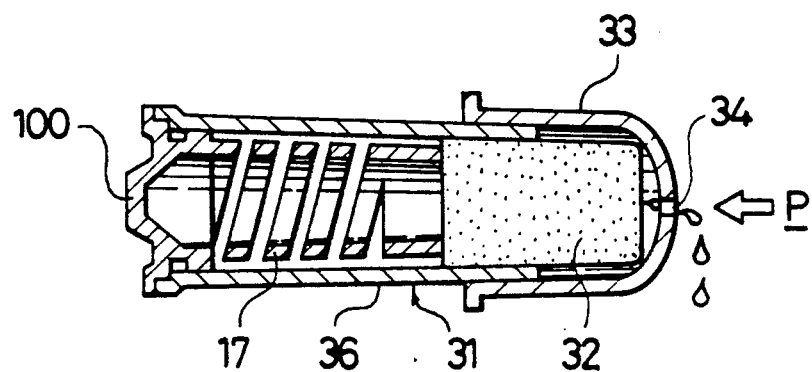
FIG. 4 is a sectional view of a third embodiment of the present invention.

A medical liquid agent applicator 30 shown in FIG. 4 has a container 31 and an applicator member 32, as in the cases of the applicators 10 and 20 described before. The applicator member 32 is mounted for movement into and out of the container 31 and is outwardly biased by the spring 17 which is integral with the bottom plate 100. The liquid agent in the container 31 is caused to exude to the surface of the applicator member 32 outside the container as the applicator member 32 is pressed into the container 21 against the force of the spring 17.

Figure 5:
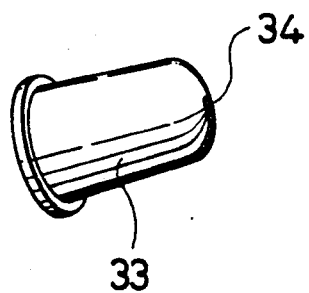
FIG. 5 is a perspective view of a liquid dripping member.
Figure 6:
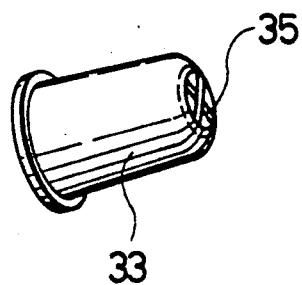
FIG. 6 is a perspective view of another liquid dripping members.

The container 30 of this embodiment is further provided with a dripping member 33. As shown in FIGS. 5 and 6, the dripping member 33 is a cap-like member having a dripping port 34 or 35 in the end thereof. When fitted on the container 31, the dripping member 33 is movable in response to a pressure P with the applicator member 32 held therein, so as to cause the applicator member 32 to move into and out of the container body 31.

In this applicator 30, therefore, it is possible to drip the liquid in the applicator 30 onto the affected part of a living body without requiring the applicator member to be touched by the user's hand after exposure of a part of the applicator member 32. Namely, when the condition of the affected part does not allow a direct contact by the applicator member 32, it is possible to use the dripping member 33 in such a manner as to cover the entire port or a portion of the applicator member 32. When the dripping member 33 is shaped to cover the entire area of the applicator member 32, the dripping member 32 is provided with at least one communication port 34 or 35. In use, the dripping member 33 is fitted on the applicator member 32 and is pressed so that the liquid agent drips onto the affected part through the communication port 34 or 35 in the dripping member 33.

In the medical applicators 10, 20 and 30 described above, the containers 11, 21 and 31 may have an ointment storage portion provided in the container body 13, 24, 36, sealing member 14 or the cap 25.

INDUSTRIAL APPLICABILITY

The present invention provides a liquid applicator having a container of any desired volume and made of a rigid and hard material and which allows only a predetermined quantity of the liquid to exude to the outer surface of the container and be spread properly and effectively over a objective part. As described above, a dripping member may be provided to enable dripping of the liquid onto a body part.

In another preferred form of the invention, the container body and the sealing member are formed integrally with each other in such a manner such as to be easily separated when the applicator is used, thus ensuring a complete hermetic seal during storage and easy opening at the time of use.

Consequently, the liquid applicator of the present invention can find a wide use, besides the application of medical liquid agents. For example, it can be used as an applicator for applying a cosmetic liquid such as a manicure liquid, a lip cream or eye liner an applicator for applying an office-use liquid such as a paste and a correction liquid, as well as a marking and painting liquid, an applicator for applying a cooking oil or the like to a cooking instrument, an applicator of a liquid for machining such as a lubricant, and applicators of various other liquids such as a wax, detergent, shoe-shining cream, and so on.

We claim:

1. A liquid applicator comprising:
   a container containing a liquid;
   an applicator member held on said container and including means for applying said liquid to an object;
   said applicator member being mounted for movement into and out of said container;
   biasing means for outwardly biasing said applicator member in a direction outwardly of said container, such that when said applicator member is pressed into said container against the force of said biasing means, the liquid is caused to exude to a surface of said applicator member outside said container;
   said container including a rigid container body containing said liquid and having an openable end; and a sealing member for sealing the openable end of said container body;
   said biasing means including an urging member housed in said container body;
   said sealing member and said container body being formed integrally with each other and with a breakable thin-walled portion formed between said container body and said sealing member, such that said sealing member and said container body can be separated when said liquid applicator is put to use; and
   said applicator member being held on said container body such that a portion of said applicator member is exposed through said openable end of said container body which is opened after separation of said sealing member from said container body.

2. A liquid applicator according to claim 1, wherein said applicator member is made of a material permeable to said liquid.

3. A liquid applicator according to claim 1, wherein the end of said sealing member opposite to the end where said sealing member integrated with said container body is so shaped as to fit to said container body after said sealing member is separated from said container body.

4. A liquid applicator according to claim 1, wherein said container has an ointment storage portion.

5. A liquid applicator according to claim 1, wherein said container body is made of glass.

6. A liquid applicator according to claim 1, wherein said container body is made of a hard plastic material.

7. A liquid applicator comprising:
   a container containing a liquid;
   an applicator member held on said container and including means for applying said liquid to an object;
   said applicator member being mounted for movement into and out of said container;
   biasing means for outwardly biasing said applicator member in a direction outwardly of said container, such that when said applicator member is pressed into said container against the force of said biasing means, the liquid is caused to exude to a surface of said applicator member outside said container;
   said container including a rigid container body containing said liquid and having an openable end; and a sealing member for sealing the openable end of said container body;
   said biasing means including an urging member housed in said container body;
   said sealing member and said container body being formed integrally with each other and with a rupturable thin-walled portion formed between said container body and said sealing member, such that said sealing member and said container body can be separated when said liquid applicator is put to use;
   said applicator member being held on said container body such that a portion of said applicator member is exposed through said openable end of said container body which is opened after separation of said sealing member from said container body; and
   a liquid dripping member including a cap-type member having a small port for dripping said liquid formed in an end portion thereof, said liquid dripping member, after said separation of said sealing member, being fitted on said container with said applicator member held therein so as to allow said applicator member to move into and out of said container.

8. A liquid applicator according to claim 7, wherein said applicator member is made of a material permeable to said liquid.

9. A liquid applicator according to claim 7, wherein the end of said sealing member opposite to the end where said sealing member integrated with said container body is so shaped as to fit to said container body after said sealing member is separated from said container body.

10. A liquid applicator according to claim 7, wherein said container has an ointment storage portion.

11. A liquid applicator according to claim 7, wherein said container body is made of glass.

12. A liquid applicator according to claim 7, wherein said container body is made of a hard plastic material.

* * * * *